US010688264B2

(12) United States Patent
Manning

(10) Patent No.: US 10,688,264 B2
(45) Date of Patent: Jun. 23, 2020

(54) CPAP COMFORT SEAL

(71) Applicant: Diana Manning, Hualapai, AZ (US)

(72) Inventor: Diana Manning, Hualapai, AZ (US)

( * ) Notice: Subject to any disclaimer, the term of this patent is extended or adjusted under 35 U.S.C. 154(b) by 420 days.

(21) Appl. No.: 15/583,385

(22) Filed: May 1, 2017

(65) Prior Publication Data
US 2017/0312466 A1 Nov. 2, 2017

Related U.S. Application Data

(60) Provisional application No. 62/330,410, filed on May 2, 2016.

(51) Int. Cl.
A61M 16/06 (2006.01)

(52) U.S. Cl.
CPC ......... A61M 16/0616 (2014.02); A61M 16/06 (2013.01); A61M 2205/02 (2013.01)

(58) Field of Classification Search
CPC .............. A61M 16/06; A61M 16/0605; A61M 16/0611; A61M 16/0616; A61M 16/0622; A61M 16/0666; A61M 16/0672; A61M 16/0683
See application file for complete search history.

(56) References Cited

U.S. PATENT DOCUMENTS

| 4,337,767 | A | * | 7/1982 | Yahata | A61M 16/0683 128/206.28 |
| 5,243,971 | A | | 9/1993 | Sullivan et al. | |
| 5,592,696 | A | * | 1/1997 | Oliver | A42B 1/02 2/175.3 |
| 6,698,427 | B1 | * | 3/2004 | Clowers | A61M 16/06 128/200.24 |
| 8,353,293 | B1 | * | 1/2013 | Fuhrman | A61M 16/06 128/204.18 |
| 8,365,733 | B2 | | 2/2013 | Rutan | |
| 2006/0081251 | A1 | * | 4/2006 | Hernandez | A61M 16/06 128/206.21 |
| 2009/0139525 | A1 | | 6/2009 | Schirm | |
| 2010/0258132 | A1 | * | 10/2010 | Moore | A61M 16/0683 128/207.11 |

(Continued)

OTHER PUBLICATIONS

CPAP Comfort Cover, retrieved from http://cpapcomfortcover.com/american-made-article-pictures/ which date Apr. 13, 2016 (Year: 2016).*

(Continued)

Primary Examiner — Joseph D. Boecker
(74) Attorney, Agent, or Firm — Boudwin Intellectual Property; Daniel Boudwin

(57) ABSTRACT

A CPAP comfort seal. The CPAP comfort seal includes a base comprising a first loop of fabric secured to a second loop of fabric, wherein the first loop of fabric and the second loop of fabric are secured to one another along a common perimeter edge. An opening is defined by an inner perimeter edge of the first loop of fabric and the second loop of fabric. An elastic band is disposed on the inner perimeter edge of the second loop of fabric. The opening is configured to receive a CPAP mask therethrough, such that elastic band contacts an outer side of the CPAP mask. The first loop of fabric contacts the wearer's face when the CPAP mask is secured thereto, providing additional sealing properties and increased comfort for the wearer.

11 Claims, 4 Drawing Sheets

(56) References Cited

U.S. PATENT DOCUMENTS

| | | | |
|---|---|---|---|
| 2011/0005524 A1 | 1/2011 | Veliss et al. | |
| 2014/0000615 A1 | 1/2014 | Wanderer | |
| 2014/0251334 A1* | 9/2014 | Kramer | A61M 16/0875 |
| | | | 128/205.25 |
| 2015/0352307 A1* | 12/2015 | Rutan | A62B 18/08 |
| | | | 128/206.24 |
| 2016/0213872 A1* | 7/2016 | Paulk | A61M 16/0605 |
| 2018/0043120 A1* | 2/2018 | Hunley | A61M 16/06 |
| 2019/0160248 A1* | 5/2019 | McPhail | A61M 16/0611 |

OTHER PUBLICATIONS

Pad a Cheek, retrieved from http://www.padacheek.com/PAC_Maskliners.html with date Apr. 13, 2016 (Year: 2016).*

* cited by examiner

CPAP COMFORT SEAL

CROSS REFERENCE TO RELATED APPLICATIONS

This application claims the benefit of U.S. Provisional Application No. 62/330,410 filed on May 2, 2016. The above identified patent application is herein incorporated by reference in its entirety to provide continuity of disclosure.

FIELD OF THE INVENTION

The present invention relates to CPAP mask seals. More specifically, the present invention provides a CPAP comfort seal having a fabric layer that comfortably seals a CPAP mask against the wearer's face.

BACKGROUND OF THE INVENTION

Many individuals must utilize a continuous positive airway pressure (CPAP) mask at night in order to alleviate the symptoms of sleep apnea. CPAP masks continuously provide air pressure in order to keep the wearer's airways open, preventing snoring and sleep disruption while ensuring the wearer does not stop breathing while sleeping.

One drawback to CPAP masks is that they are typically very uncomfortable to wear. CPAP masks have a seal that contacts the wearer's face, which is usually made from plastic. The plastic can be uncomfortable and irritating as it contacts the face. This leads to many individuals who would benefit from a CPAP mask choosing to forgo wearing the mask. This can lead to disrupted sleep or stoppage of breath, which can lead to discomfort, injury, or even death in extreme cases.

An additional problem with CPAP masks is that they often fail to properly seal against the wearer's face, which causes air to escape from the mask rather than being sent into the wearer's airway. Such an improper seal does not allow for continuous airflow and may cause the wearer to experience sleep apnea even when wearing the CPAP mask. In light of the above concerns, it is therefore desirable to provide a CPAP comfort seal that is configured to maintain an air-tight seal between the mask and the wearer's face which provides additional cushioning and comfort to the wearer.

In light of the drawbacks of CPAP devices disclosed in the prior art, it is submitted that the present invention substantially diverges in design elements from the prior art and consequently it is clear that there is a need in the art for an improvement to existing CPAP devices by providing a CPAP mask comfort seal. In this regard the present invention substantially fulfills these needs.

SUMMARY OF THE INVENTION

In view of the foregoing disadvantages inherent in the known types of CPAP mask seals now present in the prior art, the present invention provides a CPAP mask seal wherein the same can be utilized for providing convenience and comfort for a CPAP mask user. The CPAP comfort seal The CPAP comfort seal includes a base comprising a first loop of fabric secured to a second loop of fabric, wherein the first loop of fabric and the second loop of fabric are secured to one another along a common perimeter edge. An opening is defined by an inner perimeter edge of the first loop of fabric and the second loop of fabric. An elastic band is disposed on the inner perimeter edge of the second loop of fabric. The opening is configured to receive a CPAP mask therethrough, such that elastic band contacts an outer side of the CPAP mask. The first loop of fabric contacts the wearer's face when the CPAP mask is secured thereto, providing additional sealing properties and increased comfort for the wearer.

One object of the present invention is to provide a CPAP mask seal composed of materials that provides additional comfort to the wearer of a CPAP mask.

Another object of the present invention is to provide a CPAP mask seal with different designs to suit the wearer's aesthetic preferences.

A further object of the present invention is to provide a CPAP mask seal that varies in size so as to be securable to different types and sizes of CPAP masks.

Other objects, features, and advantages of the present invention will become apparent from the following detailed description taken in conjunction with the accompanying drawings.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
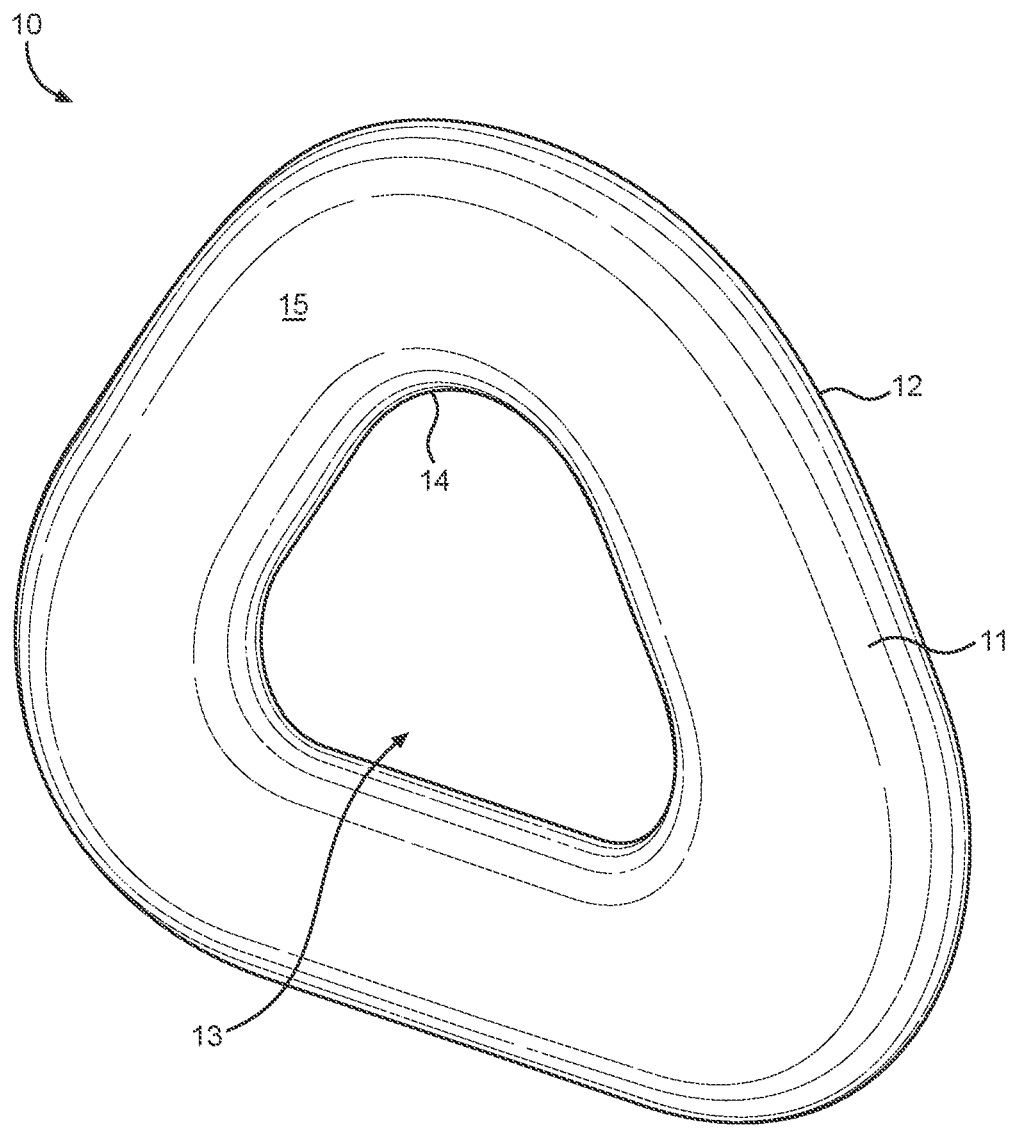
FIG. 1 shows a perspective view of a first side of the CPAP comfort seal.

Reference is made herein to the attached drawings. Like reference numerals are used throughout the drawings to depict like or similar elements of the CPAP comfort seal. For the purposes of presenting a brief and clear description of the present invention, the preferred embodiment will be discussed as used for providing comfort for CPAP users. The figures are intended for representative purposes only and should not be considered to be limiting in any respect.

Figure 2:
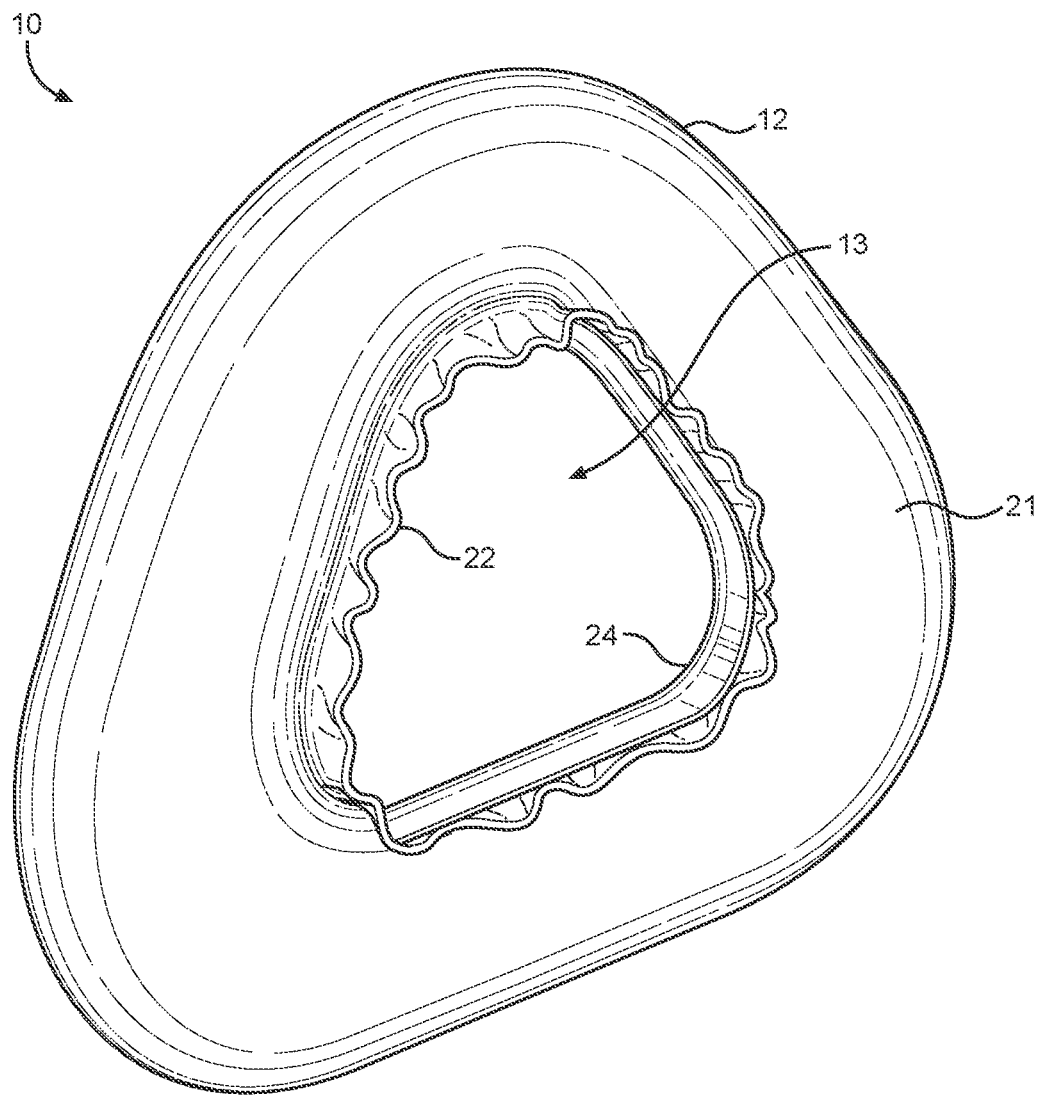
FIG. 2 shows a perspective view of a second side of the CPAP comfort seal.

Referring now to FIGS. 1 and 2, there is shown perspective view of a first side of the CPAP comfort seal and a perspective view of a second side of the CPAP comfort seal, respectively. The CPAP comfort seal comprises a base 10 that includes a first side defined by a first loop of fabric 11 secured to a second side defined by a second loop of fabric 21. The first and second loops of fabric 11, 21 may be composed of fleece, flannel, or any other comfortable fabric. The first and second loops of fabric 11, 21 are secured to one another along a common perimeter edge 12. In the illustrated embodiment, the first and second loops of fabric 11, 21 each have a uniform width.

An opening 13 is defined by an inner perimeter edge 14 of the first loop of fabric 11 and an inner perimeter edge 24 of the second loop of fabric 21. The opening 13 is sized to receive a CPAP mask therethrough, such than an inner portion of the second loop of fabric 21 contacts the mask exterior and an inner portion of the first loop of fabric 11 contacts the mask interior, while an surface 15 of the first loop of fabric contacts the wearer's face. The outer surface 15 of the first loop of fabric 11 is substantially planar so as to properly create a seal against the wearer's face. The size of the opening 13 can vary to accommodate different sizes of CPAP masks. Additionally, the opening 13 may be circular, triangular, rectangular, or any other shape as necessary for compatibility with a particular type of CPAP mask. For example, the opening 13 can be sized to fit a full face mask, an *Amara* view mask, a nasal pillow mask, a Liberty mask, or any other type or size of CPAP mask.

Figure 3:
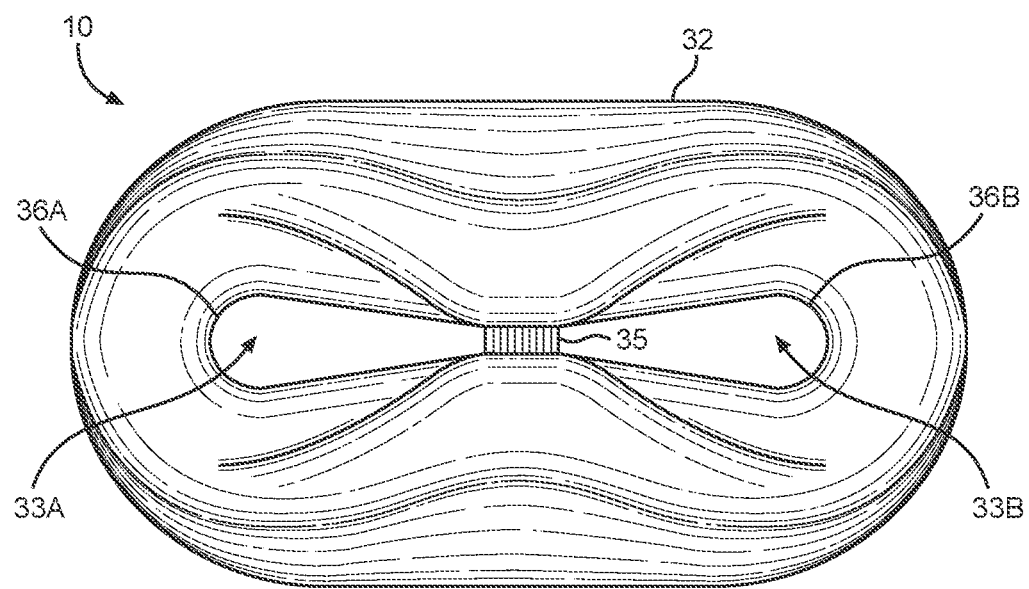
FIG. 3 shows a perspective view of an alternate embodiment of the CPAP comfort seal.

Referring now to FIG. 3, there is shown a perspective view of an alternate embodiment of the CPAP comfort seal. In the shown embodiment, the CPAP comfort seal is configured to be used with a Nasal Pillow mask. In this embodiment, a connector 35 extends across the opening, such that the opening is divided into a first opening 33A adjacent a second opening 33B. The perimeter 36A of the first opening 33A and the perimeter 36B of the second opening 33B are equal, such that the first and second openings 33A, 33B are symmetrical. In this embodiment, the perimeter edge 32 of the base 10 is elliptical. In other embodiments, the perimeter edge 32 of the base 10 may be triangular, circular, rectangular, or any other shape in order to properly conform to a particular type and size of CPAP mask.

Figure 4:
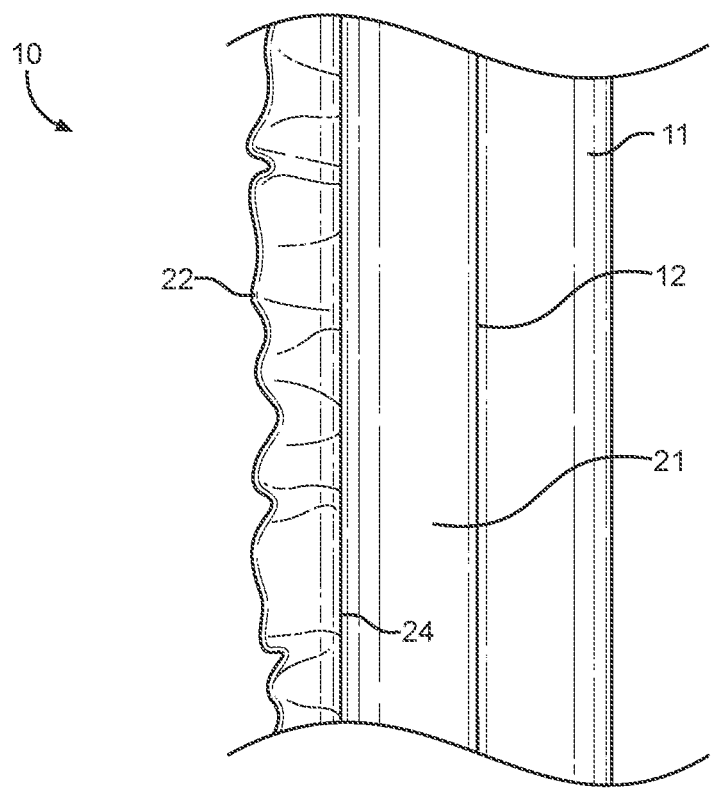
FIG. 4 shows a side view of the CPAP comfort seal.

Referring now to FIG. 4, there is shown a side view of the CPAP comfort seal. The first loop of fabric 11 is secured to the second loop of fabric 21 along a common perimeter edge 12. The first and second loops of fabric 11, 21 can be secured to one another via stitching or any other known attachment means. The elastic portion 22 may be integral to the inner perimeter edge 24 of the second loop of fabric 21 or may be secured thereto via stitching or other known attachment means.

Figure 5:
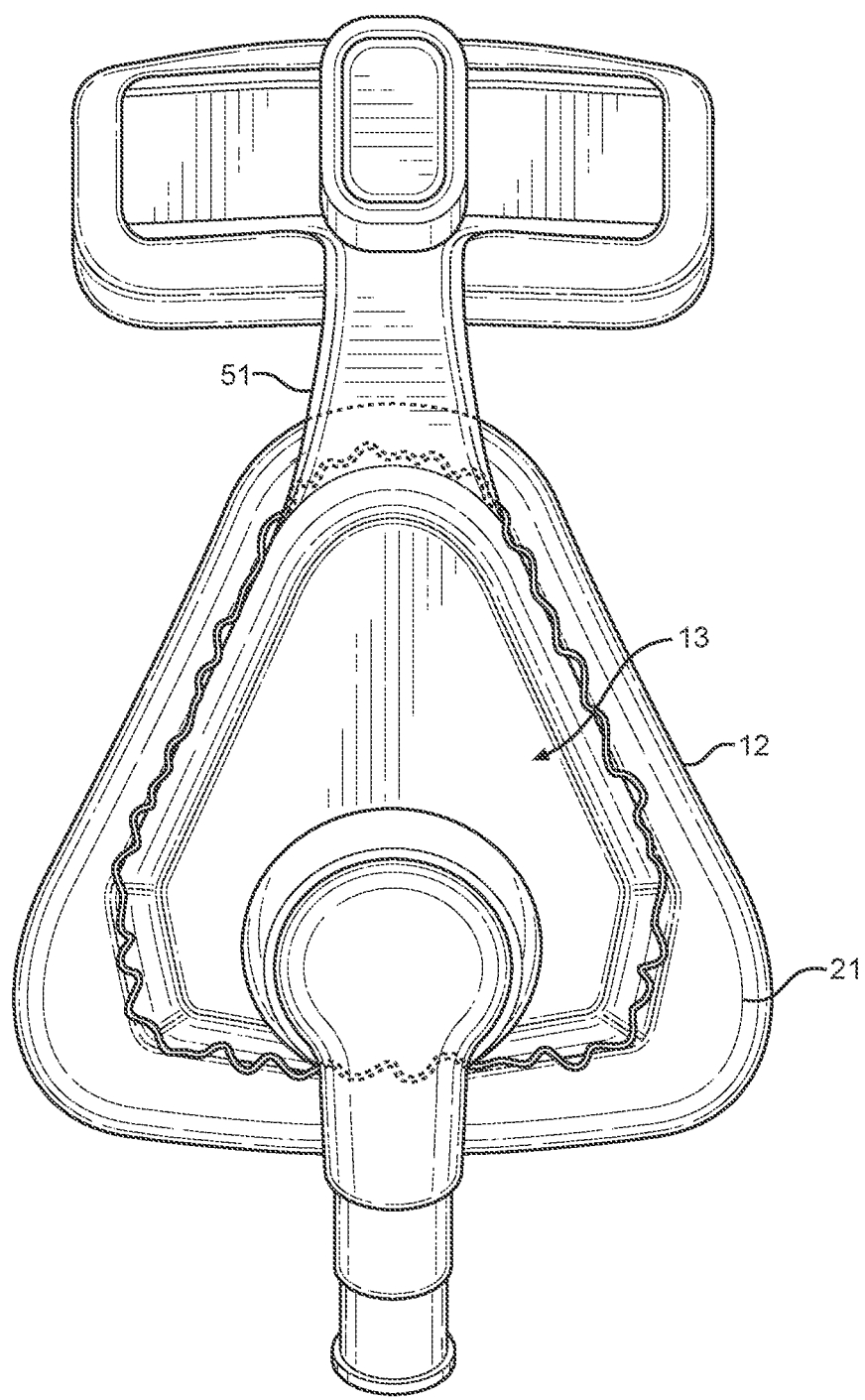
FIG. 5 shows a perspective view of the CPAP comfort seal secured to a CPAP mask.

Referring now to FIG. 5, there is shown a perspective view of the CPAP comfort seal secured to a CPAP mask. The oxygen tube portion of the CPAP mask 51 extends outward from the opening 13. The perimeter edge 12 is sized so the CPAP comfort seal makes uniform contact with the CPAP mask 51, while the elastic 22 ensures that the CPAP comfort seal remains secured to the CPAP mask 51. An inner portion of the second loop of fabric 21 contacts the mask exterior, while an inner portion of the first loop of fabric 11 contacts the mask interior. The outer surface of the first loop of fabric 11 contacts the wearer's face and effectively seals the CPAP mask thereagainst, while the comfortable fabric provides comfort for the wearer.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A CPAP comfort seal, comprising:
    a base comprising a first loop of fabric secured to a second loop of fabric, wherein the first loop of fabric and the second loop of fabric are secured to one another along a common perimeter edge;
    an opening defined by an inner perimeter edge of both the first loop of fabric and the second loop of fabric;
    an elastic band disposed on and connected to the inner perimeter edge of the second loop of fabric and extending inwardly toward the opening;
    wherein the opening is configured to receive a CPAP mask therethrough, such that the elastic band couples to an outer side of the CPAP mask;
    wherein the first loop of fabric is configured to contact a face of a wearer when the CPAP mask is secured thereto.

2. The CPAP comfort seal of claim 1, wherein the first loop of fabric and the second loop of fabric comprise a uniform width.

3. The CPAP comfort seal of claim 1, wherein the first loop of fabric is secured to the second loop of fabric via stitching.

4. The CPAP comfort seal of claim 1, wherein a surface of the first loop of fabric is substantially planar.

5. The CPAP comfort seal of claim 1, further comprising a connector that extends across the inner perimeter edge such that the opening is divided into a first opening and a second opening.

6. The CPAP comfort seal of claim 5, wherein the first opening and the second opening are symmetrical.

7. The CPAP comfort seal of claim 1, wherein the opening is circular.

8. The CPAP comfort seal of claim 1, wherein the opening is triangular.

9. The CPAP comfort seal of claim 1, wherein the opening is rectangular.

10. The CPAP comfort seal of claim 1, wherein the base is composed of fleece.

11. The CPAP comfort seal of claim 1, wherein the base is composed of flannel.

* * * * *